US00PP20915P3

(12) United States Plant Patent
Dressel

(10) Patent No.: US PP20,915 P3
(45) Date of Patent: Apr. 6, 2010

(54) GRAPEVINE PLANT NAMED 'CABERNET DORE'

(50) Latin Name: *Vitis vinifera*
Varietal Denomination: Cabernet Doré

(76) Inventor: Lucian W. Dressel, RR 2, Suite 207, Carrollton, IL (US) 62016

( * ) Notice: Subject to any disclaimer, the term of this patent is extended or adjusted under 35 U.S.C. 154(b) by 0 days.

(21) Appl. No.: 11/978,502

(22) Filed: Oct. 30, 2007

(65) Prior Publication Data

US 2009/0113578 P1 Apr. 30, 2009

(51) Int. Cl.
*A01H 5/00* (2006.01)

(52) U.S. Cl. ..... Plt./207

(58) Field of Classification Search ..... Plt./207, Plt./205

See application file for complete search history.

*Primary Examiner*—Kent L Bell

(57) ABSTRACT

A new and distinct, self rooted, variety of grapevine plant, 'Cabernet Doré', from a cross of 'Cabernet Sauvignon' and 'Norton', which can be distinguished by its outstanding wine combined with high productivity, disease resistance, and cold hardiness superior to one of its two acclaimed parents 'Cabernet Sauvignon'.

4 Drawing Sheets

Botanical classification: *Vitis vinifera.* ('Cabernet Sauvignon' crossed with 'Norton')

Varietal Denomination: 'Cabernet Doré'.

BACKGROUND OF THE INVENTION

Most grape varieties used for production of high quality wines around the world are of the species *Vitis Vinifera*. These *V. vinifera* varieties, when cultivated in northern regions of the United States with a continental climate are often subject to serious injury or death from low temperatures during winter. *V. vinifera* must also be grafted onto an American rootstock in order to be grown successfully. Although several wild *Vitis* species occur in colder regions of North America and eastern Asia, the wine made from these species generally has serious defects. Thus, a great need existed for grape plants that would combine the superior wine quality of *V. vinifera* with the cold weather resistance and disease resistance of wild species yet be free of their unpleasant wild flavors. A grape breeding program conducted by Lucian W. Dressel at Davis, Calif. and at Winters, Calif. from 2000 to 2002 developed such varieties by combining various *V. vinifera* with the native grape plant known as 'Norton' (aka 'Cynthiana', aka 'Virginia Seedling').

BRIEF SUMMARY OF THE INVENTION

The invention is a new and distinct variety of grape plant designated 'Cabernet Doré' which produces yellow to golden fruit highly suitable for white wine production, and has a combination of high wine quality, excellent cold hardiness, disease resistance, good productivity, and does not need to be grafted. It has proven to be well adapted to various states including California, Missouri, Illinois, and Kentucky. 'Cabernet Doré' resulted from a cross of 'Cabernet Sauvignon' and 'Norton' made in 2001 in Winters, Calif.

Although both parents produce black skinned grapes, it is not at all unusual for crosses to be white (or visa versa) since almost all wine grapes are highly inbred and contain recessive genes from many different forbearers. One of Cabernet Sauvignon's parents is 'Sauvignon Blanc', a white grape, and 'Norton' very likely has a white parent as well.

'Cabernet Doré' propagates moderately well from hardwood cuttings. Once rooted however the young plants quickly become established and all 'Cabernet Doré' plants propagated in this manner have been genetically stable, producing only white fruit with light golden juice. The vines of 'Cabernet Doré' have an abundance of tendrils and easily adapt themselves to a high wire cordon trellis system. Canes have a drooping growth attitude and are easily combed and trained. The bud break and bloom of 'Cabernet Doré' are very late, typically after that of both 'Cabernet Sauvignon' and 'Norton'. Its flowers are perfect and self fertile. 'Cabernet Doré' vines typically set a moderate crop. The fruit of 'Cabernet Doré' is borne on small to medium sized clusters that are tight, compact and conical to triangular in shape. The peduncles are 'Norton'-like, being quite long. The berries are small to medium in size with a waxy bloom at maturity. Berry splitting and bunch rot have not been observed to date, nor has crown gall. In commercial vineyards on a normal spray schedule no disease problems have been noted from Black Rot, Downey Mildew, Powdery Mildew, or any other fungus disease or insects. Resistance to Pierce's Disease is unknown, but is being tested in Louisiana.

The fruit of 'Cabernet Doré' can be fermented to produce a dry white wine that can be sold soon after finishing or barrel aged to produce a more complex wine. The wine has none of the flavors associated with wines made from either French *Hybrid* grapes or *V. labrusca* varieties. Cabernet Doré's wine is a light pleasant golden color. The flavors are tropical, concentrated, persistent, and immediate, with dried pineapple and papayas also with hints of allspice, nutmeg and an occasional whiff of banana.

'Cabernet Doré' is much more cold-hardy than its parent 'Cabernet Sauvignon' and has the advantage of being self rooted so that even if the plant is killed to the ground it can be renewed from an underground sucker, unlike 'Cabernet Sauvignon'. Unlike its other parent, 'Norton', its growth habits are quite orderly and manageable, and 'Cabernet Doré' does not have to be grown on a double curtain system to be profitable.

BRIEF DESCRIPTION OF THE FIGURES

FIG. 1 —'Cabernet Doré' Front—A photograph showing the front view of a 'Cabernet Doré' leaf.

FIG. 2 —'Cabernet Doré' Leaf—A photograph showing the rear view of a 'Cabernet Doré' leaf.

FIG. 3 —'Cabernet Doré' Vines—A photograph showing trunk, canes, leaves and fruit after verasion in 2006.

FIG. 4 —'Cabernet Doré' Bunches—A photograph of 'Cabernet Doré' showing a close up of three typical fruit cluster after verasion, Aug. 31, 2006.

The colors in the photographs are as close as possible with the photographic and printing technology utilized. The color values cited in the detailed botanical description accurately describe the colors of the new grape.

DETAILED BOTANICAL DESCRIPTION OF THE INVENTION

The following descriptions of 'Cabernet Doré' apply to vines planted in Carrollton, Ill. in 2004. When dimensions, sizes, colors and other characteristics are given, it is to be understood that such characteristics and approximations set forth as accurately as possible. Variations of the usual magnitude incident to climatic factors, fertilization, pruning, pest control and other cultural practices are to be expected.

Color codes used are those of The Royal Horticultural Society Colour Chart, copyrighted 2005.

VINE

General:

*Size.*—The test grapevines of 'Cabernet Doré' are planted approximately 8 feet apart down the row and 10 feet apart between the rows. The vine canopy extends from 0.75 meters to 1.0 meters out into the row. The vines were in their fourth leaf during the 2007 growing season.

*Vigor.*—When first planted, much more vigorous than 'Norton'. When mature equally vigorous as 'Cabernet Sauvignon' but without the rampant and unruly growth habits of 'Norton'.

*Productivity.*—Productive, bearing 4 tons to 6 tons per acre depending on pruning and growing conditions.

Trunk:

*Surface texture.*—Bark is loose, shaggy and peeling in long strips.

*Bark color.*—Brownish. Varies from (200A) to (202A).

*Trunk circumference.*—Very straight, round, and uniform in diameter ranging from 2.2 cm to 2.4 cm at 40 cm height from ground to 1.9 cm to 2.2 cm at 600 cm from the ground.

MATURE CANES

Size:

*Thickness.*—Canes that arise from dormant spurs vary from 6 mm to 14 mm at 5 cm to 40 cm from bud. Canes are relatively uniform in width, like 'Norton' and do not taper like 'Vidal'.

Surface: Smooth often finely striated.

Color: Canes are reddish on top (45A) and light green underneath (145A).

Internode length: Varies widely depending on type of arm, position on vine and the nature of the bud from which each cane arose. From 3 cm to 4 cm on smaller shorter arms and laterals and from 10 cm to 15 on larger canes.

Varies from 9 cm to 14 cm on the stronger upper suncanes and from 3 cm to 5 cm on lateral canes.

TENDRILS

Medium in length ranging from 10 cm to 20 cm.

*Diameter.*—Varies from 0.5 mm to 1.5 mm in thickness measured at the base of the tendril.

*Distribution.*—Discontinuous.

*Form.*—Predominately bifid, although trifid tendrils may be present.

*Color.*—Brown (N167A).

GROWING TIPS

Straight, and uniformly green (137C)

LEAVES

Mature leaves:

*General.*—Like its parent 'Norton', the leaves of 'Cabernet Doré' can have a wide variety of shapes and sizes on the same plant. Variations can be caused by the age of the vine, the location where grown, the weather and any number of other factors.

*Average leaf length.*—9 cm measured from the apex of the central lobe to the bottom of the petiole junction.

*Average leaf width.*—11 cm measured at center of leaf, 6 cm from apex and at a 45 degree angle to central vein.

*Apex of leaf.*—Length of apex 5 cm; width of apex 7 cm. Pointed tooth on top of apex averaging 1.5 cm in length. Remaining teeth on apex are medium 1.5 cm in length and 1.5 cm in width and pointed.

*Base of Leaf.*—Rounded, gradually sloping upwards, approximately 9 cm wide. General shape of petiole sinus light bulb shaped: 3.0 cm long on average mature leaf, 2.0 cm wide at base.

*Shape of upper leaf sinus.*—Large 5 cm in length, 1 cm in width at base.

*Leaf Margins.*—Serrate with irregular teeth, commonly approximately 9 teeth to 12 teeth per lobe, and approximately 45 teeth to 60 teeth on entire leaf.

*Average blade length.*—9 cm as measured from the apex of the center leaf lobe to the petiole junction.

*Size of blade.*—Small to medium, usually lobed. Often resembles a small 'Cabernet Sauvignon' leaf with overlapping superior lobes appearing to create holes in the leaf surface resembling eyes.

*Shape.*—Cuneo-truncate. Galet coordinates: 146-3-57.

*Shape of teeth along leaf margins.*—Convex.

*Length of teeth along leaf margins.*—Small to medium and variable, 2 mm to 4 mm in length.

*General shape of petiole sinus.*—Open, but spear shaped, narrowing at base.

*Shape of upper leaf sinus.*—Light bulb shaped when open. When closed has appearance of round hole in surface of leaf.

*Upper leaf surface.*—Rough (136A).

*Lower leaf surface.*—Rather dull and lighter in intensity of color (138D).

*Upper leaf veins.*—Yellowish-green (2C).

*Lower leaf veins.*—Yellow-green (2C).

*Surface texture.*—Rough.

*Surface appearance.*—Dull.

*Lower surface texture.*—Rough, dull.
*Length of petiole.*—6 cm to 8 cm.
*Petiole thickness.*—2.0 mm to 3.0 mm measured at mid petiole.
*Petiole shape.*—Round, glabrous, smooth.
*Petiole color.*—Pinkish-red (N57A).
*Length of petiole compared to mid vein.*—On average about 70%.

FLORAL CLUSTER DESCRIPTION

*Bloom timing.*—Varies widely from year to year. Generally late, slightly after 'Norton'. May 10$^{th}$ in 2006.
*Cluster form.*—Conical to triangular.
*Clusters per shoot.*—Usually three.
*Floral cluster length.*—Average 80 cm.
*Floral cluster width.*—Average 30 cm.
*Cluster peduncles.*—Length 10 cm to 12 cm, thickness 3.0 cm. to 4.0 cm.
*Cluster peduncle color.*—Light green (141A).
*Inflorescence.*—Hermaphroditic.
*Floral stamens.*—Upright with typically observed anthers 2 mm in length and 0.5 mm in width.
*Flower length.*—2 mm in average flower.
*Flower diameter.*—1 mm in average flower.
*Flower Petals.*—Five in number, and open from the bottom to the top. Remaining entire after separation. Petals ovoid in shape with 5 sections remaining attached to one another after falling to ground, 3 mm in diameter. Apex of petals is concave. Base is smooth and 2.5 mm in circumference. Margins are smooth and convexly curved. Color on top surface of petals is grass green (145C). Color on underside of petals is light green (149D).
*Sepals.*—Five in number, and commonly very poorly developed or nonexistent. If present, appearing as little more than a dusty residue with a light green color (149D).
*Pollen amount.*—Abundant.
*Pollen color.*—Pale yellow (8C).
*Calyptras separation from the flower base.*—Complete.
*Duration of bloom.*—Average 10 days to 12 days depending on ambient temperatures during the bloom period.

FRUIT DESCRIPTION—PRIMARY CLUSTERS

*Date of maturity.*—Sep. 15, 2006 in west central Illinois.
*Bunch size.*—medium.
*Bunch length.*—12 cm to 25 cm, not including the peduncle.
*Bunch width.*—10 cm to 15 cm.
*Bunch form.*—Triangular to round in shape. Usually well filled out with small to medium tight bunches.
*Bunch weight.*—Average from 90 gm to 150 gm.
*Bunch density.*—Tight like 'Norton'.
*Peduncle length.*—Medium from 3 cm to 5 cm.
*Peduncle color.*—light green (141A).
*Peduncle thickness.*—Ranges from 2.0 cm to 3.0 cm at the peduncle base.
*Berry form.*—Round.
*Cross sectional view berry form.*—Globose.
*Berry size.*—small to medium 10 mm to 12 mm in diameter.
*Berry weight.*—2 gm to 5 gm.
*Berry uniformity.*—Excellent.
*Berry pedicel color.*—very light yellow (158D).
*Berry pedicel length.*—5 mm to 6 mm.
*Berry pedicel thickness.*—1 mm to 2 mm.
*Berry pedicel length.*—5 mm to 6 mm.
*Berry pedicel thickness.*—1 mm to 2 mm.
*Attachment.*—Very strong with no shatter at commercial maturity.
*Berry skin color.*—Light yellow brown (163B). With waxy bloom berries have a whitish look.
*Berry skin thickness.*—Medium 0.75 mm.
*Berry skin surface texture.*—Smooth and glabrous.
*Berry skin, tenacity to flesh.*—Skin is tenacious to the flesh.
*Berry skin, tendency to crack.*—Has never shown any cracking.
*Berry skin, reticulation.*—Surface is smooth with no reticulations present.
*Berry flesh color.*—Light translucent yellow (158D).
*Juiciness of flesh.*—Similar to standard commercial wine varieties. Much juicier than 'Norton', not as juicy as 'Sauvignon Blanc'.
*Berry firmness.*—Relatively firm.
*Berry juice.*—clear, tart, light yellow (16C)).
*Solids-sugar percentage* (*at maturity*).—22.0 on Sep. 12, 2006.
*pH of berry juice.*—3.18 on Sep. 12, 2006.
*Titratable acidity.*—7.75 gm/liter.
*Seed.*—Viable, 3 seeds per berry to 4 seeds per berry, average size and shape for *V. vinifera*. 6.5 mm in length and 3.5 mm in width.
*Flavor.*—Good, tart, sweet, typical *V. vinifera* white wine grape flavor.
*Aroma.*—Typical crushed white wine grape aroma. No wild aromas.
*Aroma.*—Typical crushed white wine grape aroma. No wild aromas.

SECONDARY BUNCHES

Almost no secondary bunches have been observed in normal years with no spring frost.

COMPARISON BETWEEN PARENTAL AND COMMERCIAL CULTIVARS

The physical appearance of the vine of 'Cabernet Doré' more closely resembles that of its parent 'Cabernet Sauvignon'. Like 'Cabernet Sauvignon' the leaves of 'Cabernet Doré' are more modest in size and show fewer variations than do the leaves of its parent 'Norton'. The growth habits are more orderly than 'Norton' and it can produce normal crops of between 4 tons to 6 tons per acre without having to be grown on a double curtain trellis system. 'Cabernet Doré' is far more resistant to the endemic vine diseases of the eastern U.S. than 'Cabernet Sauvignon' and it can be grown on its own roots. The berries and bunches are larger than 'Norton' and the berries have fewer seeds making wine making easier.

What is claimed is:

1. A new and distinct variety of grapevine plant as illustrated and described.

* * * * *

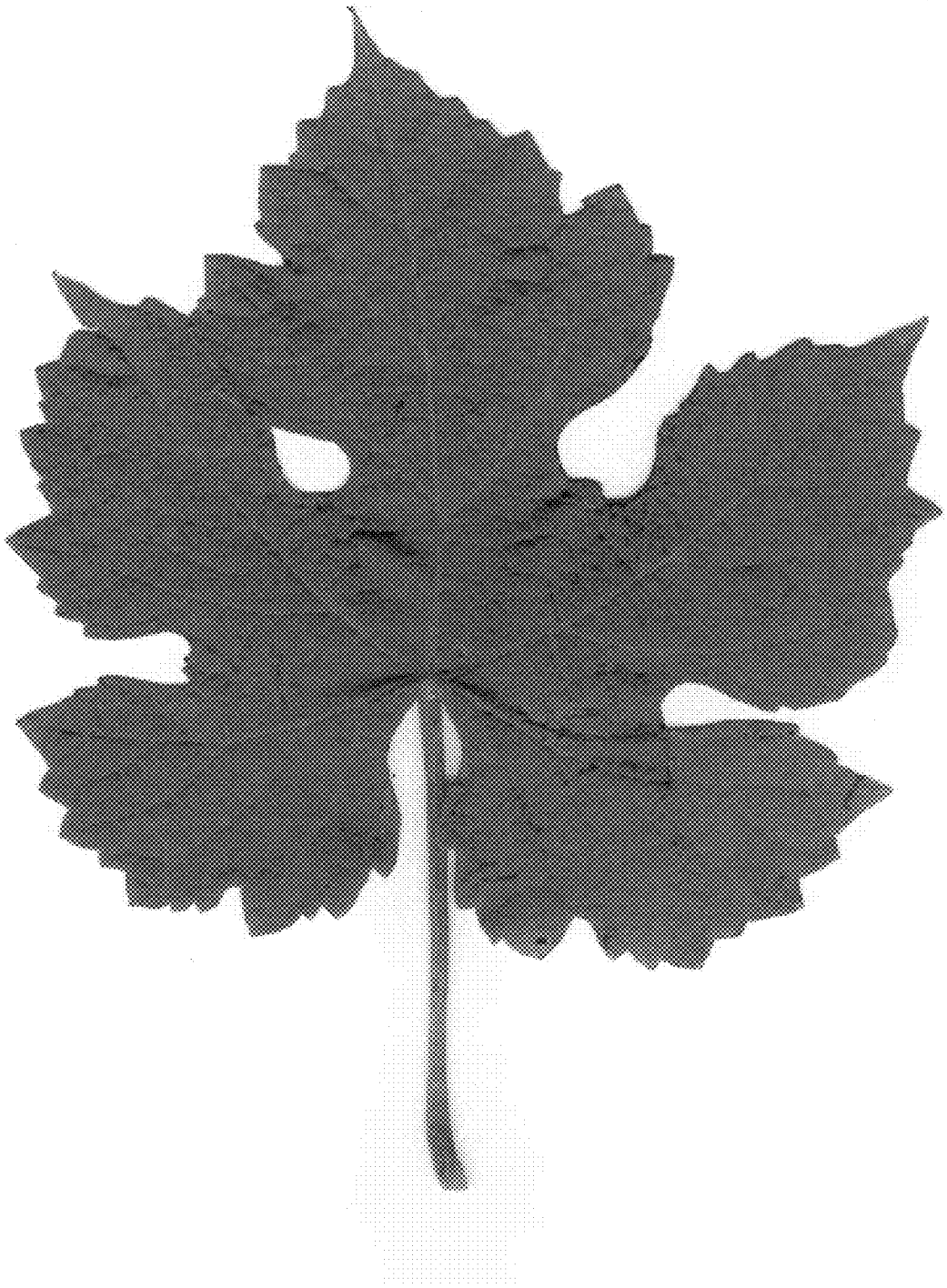

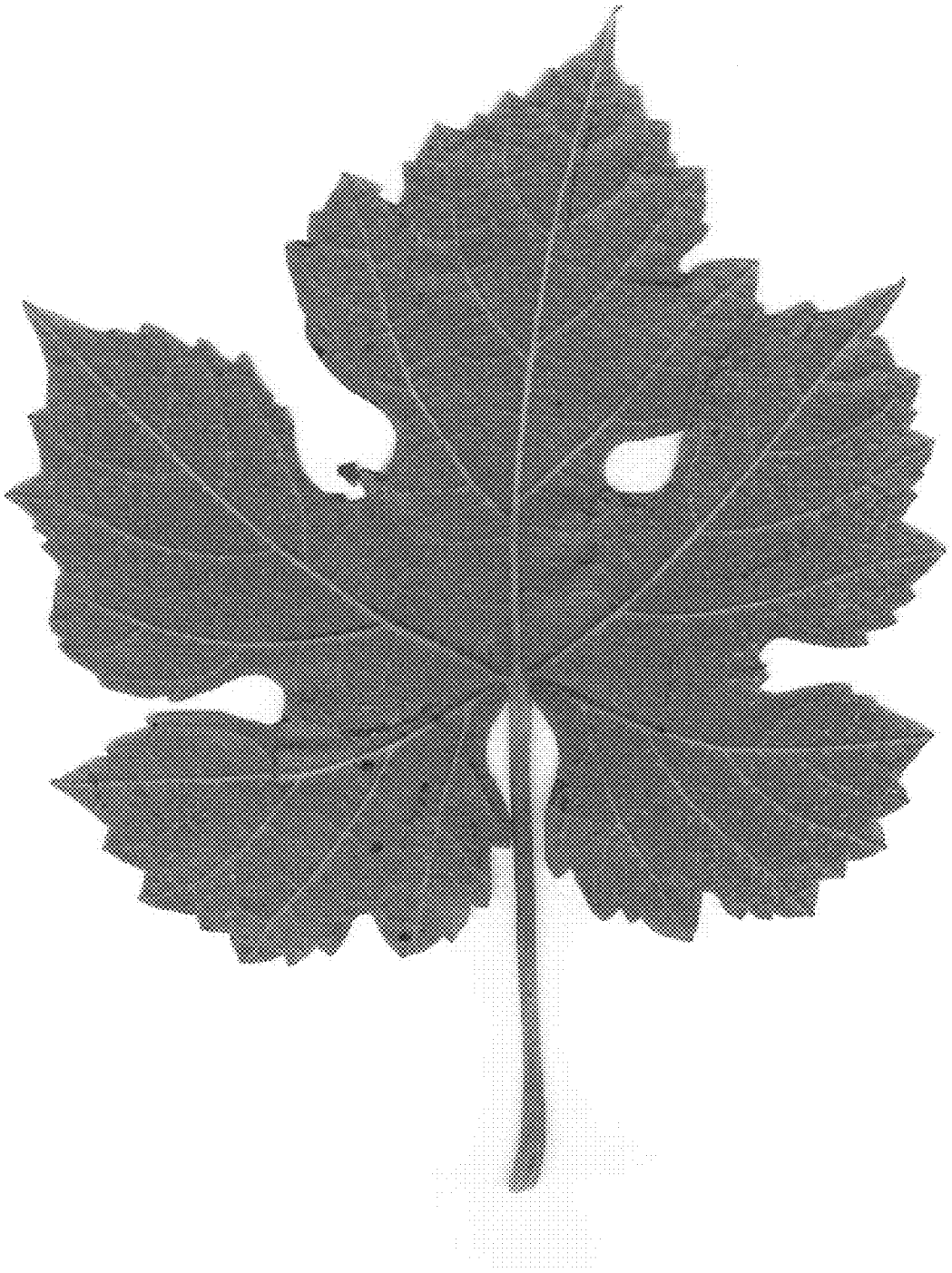

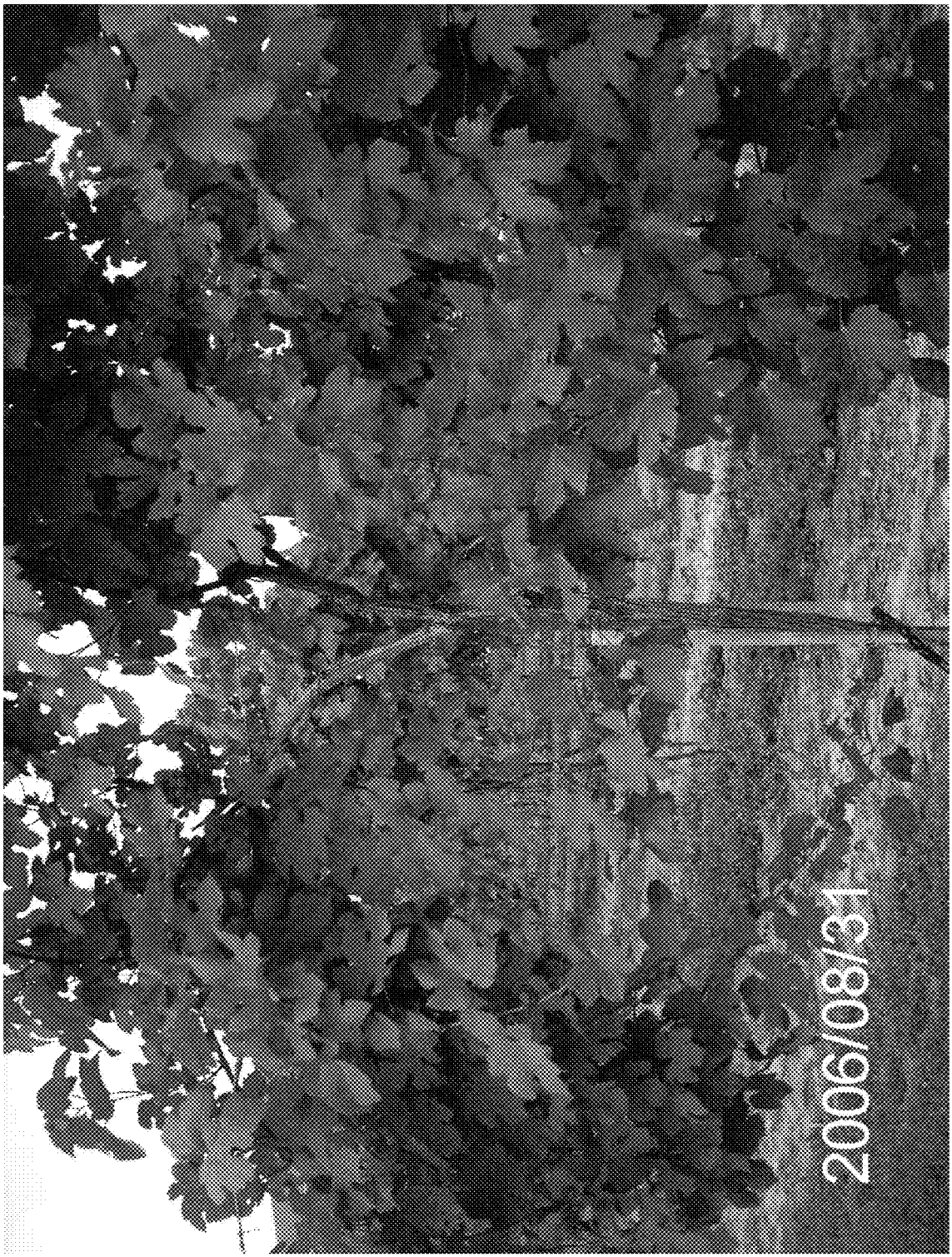
2006/08/31

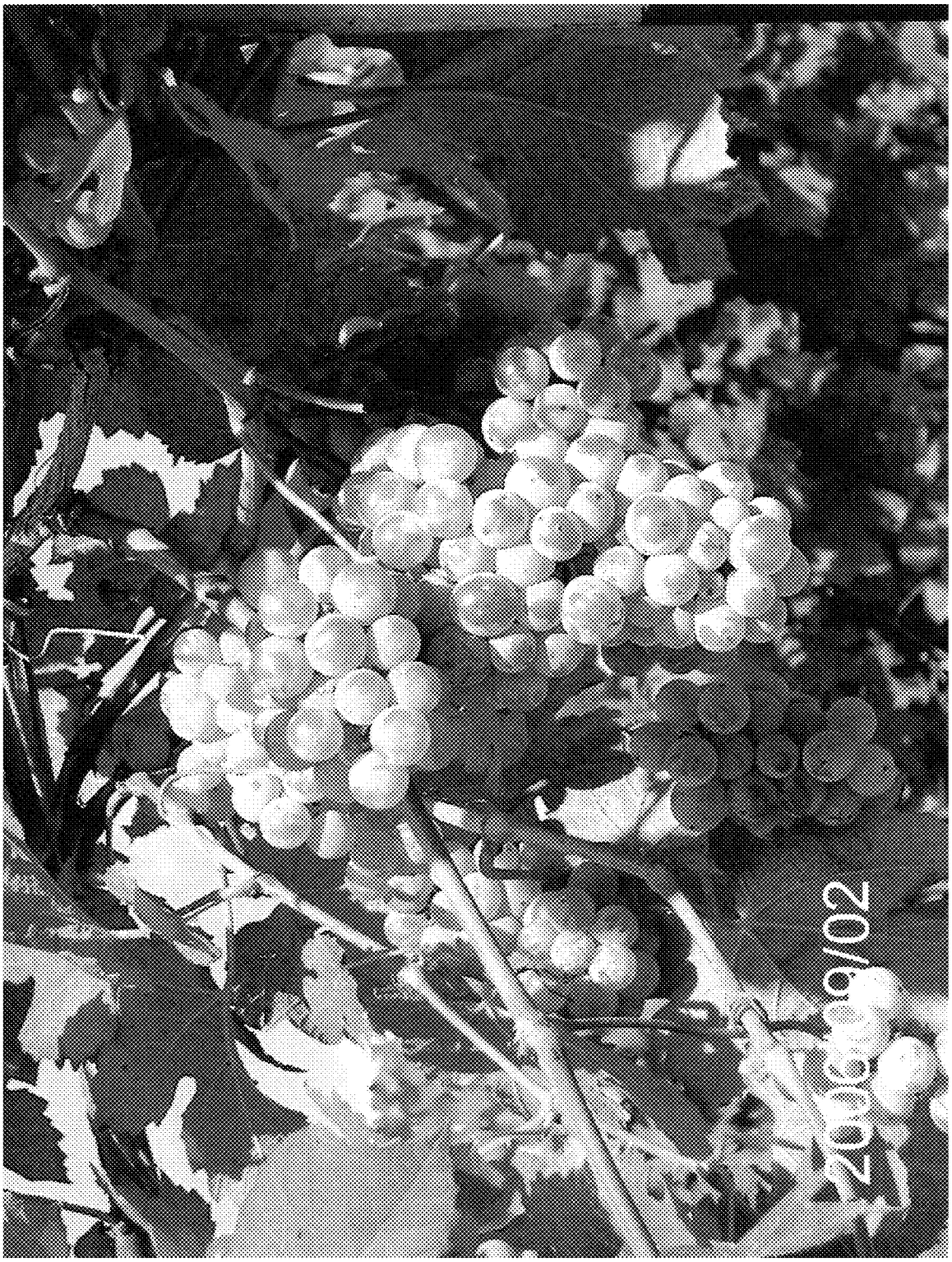
20/6/9/02